United States Patent [19]

Spaziani et al.

[11] 4,314,895
[45] Feb. 9, 1982

[54] METHOD OF MAKING LIQUID MEMBRANE ELECTRODE

[75] Inventors: Frederick F. Spaziani, Lexington; James E. Fowler, Watertown, both of Mass.

[73] Assignee: Nova Biomedical Corporation, Newton, Mass.

[21] Appl. No.: 146,092

[22] Filed: May 2, 1980

Related U.S. Application Data

[62] Division of Ser. No. 925,518, Jul. 17, 1978, Pat. No. 4,233,136.

[51] Int. Cl.³ ............... B29C 27/00; G01N 27/30
[52] U.S. Cl. .................... 204/195 M; 264/159; 264/259; 264/267
[58] Field of Search ........ 204/195 M, 195 G, 195 R, 204/195 L; 264/154, 259, 267

[56] References Cited

U.S. PATENT DOCUMENTS

| | | | |
|---|---|---|---|
| 2,378,901 | 6/1945 | Amrhein et al. | 264/274 |
| 2,932,081 | 4/1960 | Witte | 264/267 |
| 3,172,934 | 3/1965 | Krieg | 264/267 |
| 3,467,590 | 9/1969 | Gibson et al. | 204/195 L |
| 3,475,530 | 10/1969 | Cooper | 264/259 |
| 3,562,129 | 2/1971 | Simon | 204/195 M |
| 3,657,095 | 4/1972 | Tosteson | 204/195 L |
| 3,706,649 | 12/1972 | Cosgrove et al. | 204/195 M |
| 3,707,455 | 12/1972 | Derr et al. | 204/195 P |
| 3,753,887 | 8/1973 | Kedem et al. | 204/195 L |
| 3,767,553 | 10/1973 | Brown et al. | 204/195 M |
| 3,835,011 | 9/1974 | Baum et al. | 204/195 M |
| 3,855,098 | 12/1974 | Fletcher | 204/195 M |
| 3,879,279 | 4/1975 | Baucke | 204/195 G |
| 3,932,233 | 1/1976 | Ruzicka et al. | 204/195 L |
| 4,003,776 | 1/1977 | Barnes | 264/267 |
| 4,020,830 | 5/1977 | Johnson et al. | 204/195 M |
| 4,168,219 | 9/1979 | Hiio et al. | 204/195 M |
| 4,177,233 | 12/1979 | Roberts | 264/267 |

*Primary Examiner*—G. L. Kaplan

[57] ABSTRACT

An electrode assembly comprising an organic plastic sample flow-through tube, a portion of the wall of which comprises a membrane, the membrane comprising a matrix of an organic plastic material containing a non-volatile solvent-plasticizer and an ion exchange material dissolved in the solvent plasticizer, the membrane chemically bonded to and integral with said tube. The method of forming the membrane to the tube comprises dissolving the matrix material, the ion exchange material and the non-volatile solvent plasticizer in a volatile solvent, placing the resulting solution on a surface and evaporating the volatile solvent to form the membrane, contacting an edge of the tube to the membrane material, contacting the tube edge with said volatile solvent and allowing the solvent to evaporate.

2 Claims, 4 Drawing Figures

METHOD OF MAKING LIQUID MEMBRANE ELECTRODE

This is a division of application Ser. No. 925,518 filed July 17, 1978 and now U.S. Pat. No. 4,233,136.

This invention relates to electrodes for measuring ion concentrations in sample solutions and more particularly to a flow-through electrode employing a liquid membrane.

Liquid membrane electrodes are known in the art. Ion exchange occurs through an interface between an ion exchange material and the sample solution. In certain prior art systems the liquid membrane interface is maintained by a flow of solution containing the ion exchange material. This has obvious disadvantages since in a flowing sample, impingement of the sample on the electrode may destroy the liquid membrane allowing the sample to contact the electrode with deleterious effects. It has also been suggested in the prior art to contain the liquid phase of the ion exchange material in a matrix of organic plastic material such as polyvinylchloride with a suitable plasticizer which also functions as a solvent for the ion exchange material. The membrane is then cast from the solution and after being fused is mechanically held on the end of the electrode. This type arrangement also presents difficulties of sealing the membrane to the electrode. Though the advantages of a flow-through electrode employing a linear flow path for the liquid sample are known and are employed in other type electrodes, the difficulty of supporting and sealing the liquid membrane to the tube wall has been an impediment to the development of a flow-through electrode employing a liquid membrane.

Accordingly, it is a principal object of this invention to provide a linear flow-through electrode in which a portion of the wall comprises a membrane containing a liquid phase ion exchange material for the electrode. It is a further object of this invention to provide such an electrode assembly in which the membrane is integrally sealed to the wall of the flow-through tube.

The invention features the method of making the electrode comprising the steps of dissolving an organic plastic matrix material in a volatile solvent and then mixing a non-volatile solvent-plasticizer and an ion exchange material, which is soluble in the plasticizer, with the plastic material and the volatile solvent. The solution thus obtained is cast on a surface to form a membrane as the volatile solvent is evaporated. The membrane is attached to a tube of organic plastic material by contacting the tube with a volatile solvent common for the membrane and the tube and abutting the membrane material against the tube. As the solvent evaporates, the tube and membrane are integrally joined.

In a particular embodiment, an opening is formed in the tube to receive the membrane. A mandrel is inserted within the tube and across the opening. The membrane is then formed on the mandrel contacting the tube edges at the opening and the volatile solvent in the membrane contacts the tube edges thereby resulting in the joinder of the membrane to the tube as the volatile solvent evaporates.

In one embodiment for detecting potassium ions, the matrix material comprises polyvinylchloride, the ion-exchange material comprises valinomycin, the non-volatile solvent comprises 2-nitro-p-cymene and the volatile solvent comprises a tetrahydrofuran. The membrane thickness is preferably in the range of from 8–12 mils the polyvinylchloride matrix material comprises from 8–26%, preferably from 12–20%, by weight of the membrane.

Other objects, features and advantages of this invention will be apparent to those skilled in the art from the following detailed description of a preferred embodiment thereof, taken together with the accompanying drawings, in which.

Figure 1:
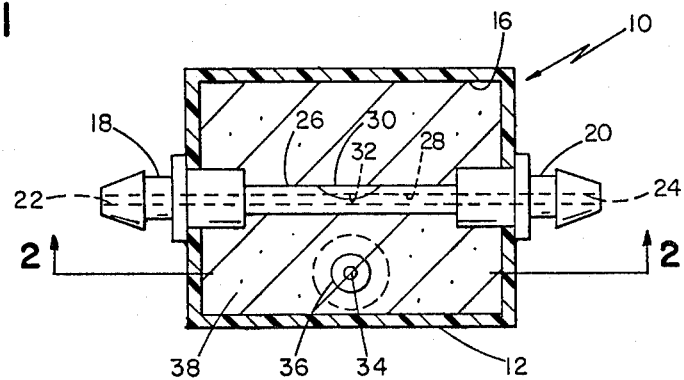
FIG. 1 is a plan view in section of an electrode assembly according to the invention.
Figure 2:
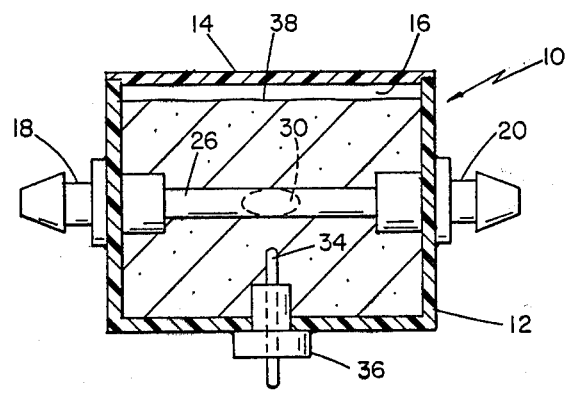
FIG. 2 is a view of the electrode assembly taken along the line 2—2 of FIG. 1.
Figure 3:
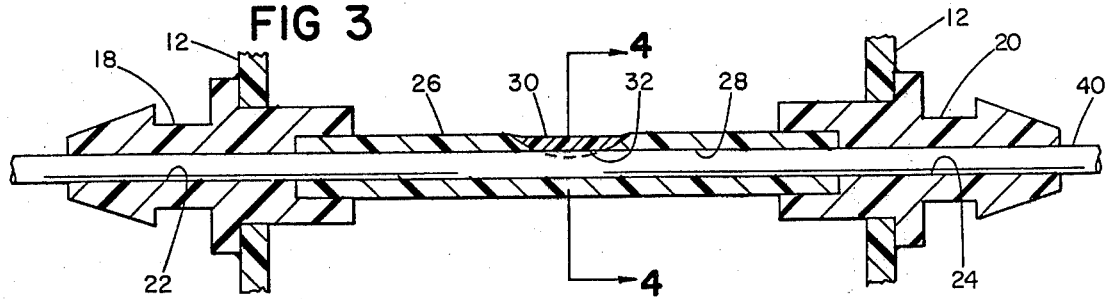
FIG. 3 is an enlarged sectional view of a portion of the electrode assembly illustrated in FIG. 1, illustrating the method of forming a membrane in the assembly.
Figure 4:
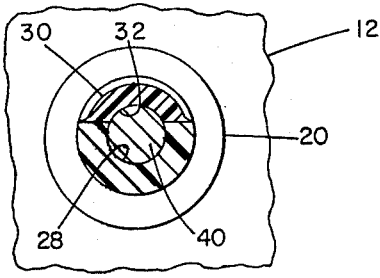
FIG. 4 is a sectional view taken along the line 4—4 of FIG. 3.

An electrode assembly 10, according the invention, is illustrated in FIGS. 1 and 2. The electrode assembly comprises a housing 12 having a cover 14 defining a closed interior chamber 16. The housing 12 and cover 14 are of rigid plastic material such as phenolics or epoxys. Axially aligned end fittings 18,20 extend through the walls of housing 12 and define nipples to receive tubing outside of the housing. Fittings 18,20 have axial bores 22,24 extending therethrough, the bores being enlarged at their ends within housing 12, best illustrated in FIG. 3. A straight section of cylindrical, preferably flexible, organic plastic tubing 26 extends between fittings 18,20 and is secured within the enlarged portions of bores 22,24. Tubing 26 has a central tubular passage 28 extending axially therealong in fluid flow communication with bores 22,24. A portion of the wall of tubing 26 is interrupted by an opening on one side thereof and contains a membrane 30. Membrane 30 is chemically bonded to and integral with tube 26. The inner surface 32 of membrane 30 conforms to the inner configuration of tubing 26 presenting a linear, smooth continuous surface defining a linear flow path for liquid samples. A silver-silver chloride reference electrode 34 and insulating fitting 36 supporting the electrode 34 extend through a wall of the electrode housing 12. The housing 12 contains a reference solution 38 in the form of a gel forming a salt bridge in contact with the outer surface of membrane 30 and with electrode 34. Housing 12, cover 14, fittings 18,20,36 and tube 26 are inert and electrically insulating.

Membrane 30 comprises an organic plastic matrix containing an ion exchange material and a non-volatile plasticizer which constitutes a solvent for the ion exchange material. The membrane materials are all soluble in a common volatile solvent. In a particular embodiment, the plastic matrix material comprises polyvinylchloride. The non-volatile solvent plasticizer comprises 2-nitro-p-cyamine. For the detection of potassium ions, the ion exchange material comprises valinomycin, the valinomycin being added to the plasticizer solvent, i.e., approximately 40 milligrams of valinomycin is added to 1.07 grams of 2-nitro-p-cymene. The polyvinylchloride matrix supports the membrane. It is important that the amount of polyvinylchloride be controlled to provide adequate support without interfering with the electrical properties of the membrane. It has been found that in the embodiment described in the polyvinylchloride may comprise in the range of from 8 to 26 percent and preferably is in the range of from 12 to 20 percent, by weight, of the membrane. Preferably, the membrane has a thickness in the range of from 8 to 12 mils.

The reference solution in the housing in a particular embodiment comprises a 0.1 M aqueous solution of potassium chloride saturated with silver chloride. Agar, e.g., 0.5%, is added to the solution to form an aqueous gel.

To make the electrode, tube 26 is first bent into a curve and a portion on the outer side of the curve is cut away to form an opening to which membrane 30 is formed. Fittings 18 and 20 are then assembled to tube 26 within housing 12. Prior to the assembly the ends of tube 26 are coated with a volatile solvent such as tetrahydrofuran. The solvent softens the fittings and tube at their abutting surfaces and results in their integral joinder after evaporation of the solvent. A mandrel 40 extends through the fittings 18,20 and through tube 26. High molecular weight polyvinylchloride polymer in powder form, having a density of 1.40 grams/cc., such as that sold by Aldridge Chemical Company of Milwaukee, Wisconsin, as Catalog No. 18956-1, is dissolved in a volatile solvent such as tetrahydrofuran to which are then added non-volatile solvent plasticizer 2-nitro-p-cymene and valinomycin. The solution thus formed, comprising a viscous slurry, is placed on the mandrel 40 contacting the edges of the opening formed in the tube. The volatile solvent, tetrahydrofuran softens tube 26 at its edges resulting in the chemical bonding of the membrane to the tube as the solvent evaporates. Evaporation is allowed to proceed under ambient conditions for about 24 hours although it may be hastened if desired by the application of mild heat, e.g., 40°-50° C. As the volatile solvent evaporates, the membrane 30 is formed integrally with tube 26 after which the mandrel 40 is withdrawn. The reference electrode 34 and fitting 36 are inserted into the housing 12. Fittings 18,20 and 36 are bonded where they contact housing 12 to seal the fittings to the housing. The chamber 16 is then filled with the reference solution 38 and cover 14 closed over chamber 16, the edges of the cover being bonded to seal the cover 14 to housing 12.

In particular examples membranes comprising 1.07 grams of 2-nitro-p-cymene, 40 milligrams of valinomycin and varying amounts of polyvinylchloride as the matrix have been constructed. The membrane materials were dissolved in about 5 cc. of tetrahydrofuran, the solution deposited on a mandrel in an opening formed in a polyvinylchloride tube, the tube having an inner diameter of 0.032 inches, the tetrahydrofuran evaporated and a membrane thus formed integrally with the tube, the membrane having a thickness of 10-12 mils and an area of 0.02 inches. Utilizing 0.1 grams, i.e., 8.3%, of polyvinylchloride in the mixture resulted in a membrane which was relatively fragile, a slope of 58.5 mv/decade change in potassium ion concentration and good analytical performance. Utilizing 0.15 grams, i.e., 11.9% of polyvinylchloride, resulted in a marginal mechanical strength for the membrane, a slope of 58.5 mv/decade and good analytical performance. Utilizing 0.24 grams, i.e., 17.8% of polyvinylchloride resulted in a more mechanically rigid membrane, a slope of 58.5 mv/decade and good analytical performance. Utilizing 0.4 grams, i.e., 26.5%, polyvinylchloride resulted in a yet more mechanically rigid membrane, a slope of 57 mv/decade and poor analytical performance.

Advantageously, an electrode assembly according to the invention supports and seals a liquid membrane integrally with the wall of the tube permitting the construction of a linear flow through liquid membrane electrode. The smooth linear flow path avoids turbulence and eddy currents as well as mechanical discontinuities which can trap portions of the liquid sample being tested and thus permits a more accurate, rapid and reliable response. The use of tubing allows a small diameter flow path minimizing the amount of sample required. The matrix support of the ion exchange material and the linear flow path eliminate the danger of rupturing the liquid membrane. The fabrication of the membrane to the flow-through tube is simple and convenient.

Other embodiments of this invention will occur to those skilled in the art which are within the scope of the following claims. By way of example the membrane may be preformed and placed on a mandrel as an annular membrane, tubes may then be contacted against each side of the membrane and solvent applied to bond the tube ends to the membrane.

What is claimed is:

1. The method of forming an ion-sensitive membrane for an electrode chemically bonded to and integral with a sample flow-through tube of organic plastic material comprising forming a membrane solution by dissolving an organic plastic matrix material, a non-volatile solvent-plasticizer and an ion exchange material in a volatile solvent which is also a solvent for said tube material, said ion exchange material being soluble in said solvent-plasticizer, placing a mandrel having a diameter equal to the inner diameter of said tube coaxially of said tube at an opening defined by an edge of said tube, placing said membrane solution on said mandrel at said opening in contact with said tube edge and allowing said volatile solvent to evaporate therefrom to form said membrane, said membrane thus formed and said tube thereby being chemically bonded to each other.

2. The method claimed in claim 1 in which said tube edge comprises the edge of an opening formed on one side of said tube, said membrane being formed across said opening.

* * * * *